(12) United States Patent
Brown et al.

(10) Patent No.: US 10,575,787 B2
(45) Date of Patent: Mar. 3, 2020

(54) HYDRATION SENSOR

(71) Applicants: Elliott R. Brown, Beavercreek, OH (US); Weidong Zhang, Cary, NC (US)

(72) Inventors: Elliott R. Brown, Beavercreek, OH (US); Weidong Zhang, Cary, NC (US)

(73) Assignee: Wright State University, Dayton, OH (US)

( * ) Notice: Subject to any disclaimer, the term of this patent is extended or adjusted under 35 U.S.C. 154(b) by 81 days.

(21) Appl. No.: 15/489,176

(22) Filed: Apr. 17, 2017

(65) Prior Publication Data

US 2018/0231475 A1 Aug. 16, 2018

Related U.S. Application Data

(60) Provisional application No. 62/458,285, filed on Feb. 13, 2017.

(51) Int. Cl.
*A61B 18/14* (2006.01)
*A61B 5/00* (2006.01)
*A61B 5/05* (2006.01)

(52) U.S. Cl.
CPC ............. *A61B 5/7228* (2013.01); *A61B 5/05* (2013.01); *A61B 5/443* (2013.01); *A61B 5/4875* (2013.01); *A61B 5/7225* (2013.01); *A61B 5/7203* (2013.01)

(58) Field of Classification Search
CPC ............... A61B 18/18; A61B 18/1815; A61B 2018/00785; A61B 2017/00154; A61B 2018/00464; A61B 2018/00577; A61B 2018/00589; G01R 27/02; G01R 27/26; G01R 27/2605; G01R 27/2652; G01R 27/2676
See application file for complete search history.

(56) References Cited

U.S. PATENT DOCUMENTS

| | | | | |
|---|---|---|---|---|
| 3,140,608 A | * | 7/1964 | Clark | G01F 23/263 331/65 |
| 4,350,982 A | * | 9/1982 | Alpers | G01S 13/767 342/201 |
| 5,548,217 A | * | 8/1996 | Gibson | A61L 2/12 324/313 |
| 9,074,922 B2 | * | 7/2015 | Dayal | G01F 23/284 |

(Continued)

*Primary Examiner* — Alesa Allgood
(74) *Attorney, Agent, or Firm* — McNees Wallace & Nurick LLC

(57) ABSTRACT

A hydration sensor is provided that includes a circulator having a plurality of ports, an amplitude-modulated coherent source connected to a first port of the circulator, a rectifier or other power sensor connected to a second port of the circulator followed by an RF baseband low-noise amplifier, a coupling structure connected to the third port of the circulator, and a demodulator connected to the output of the rectifier. The hydration sensor can include an RF low noise amplifier between the circulator and rectifier, and/or a second amplitude modulator between the circulator and the coupling structure. The coupling structure can be either a guided-wave near-field structure or an interfacial capacitive or inductive element. In the former case, the hydration is determined by measuring the reflectivity of the guided-wave radiation, and in the latter case it is determined by measuring the change of reflectivity (through change of impedance) of the interfacial element.

20 Claims, 13 Drawing Sheets

(56) References Cited

U.S. PATENT DOCUMENTS

| | | | | |
|---|---|---|---|---|
| 2010/0295744 | A1* | 11/2010 | Lofbom | H01Q 15/06 343/753 |
| 2012/0191072 | A1* | 7/2012 | Hancock | A61B 18/18 604/542 |
| 2014/0025033 | A1* | 1/2014 | Mirkov | A61B 18/20 604/501 |

* cited by examiner

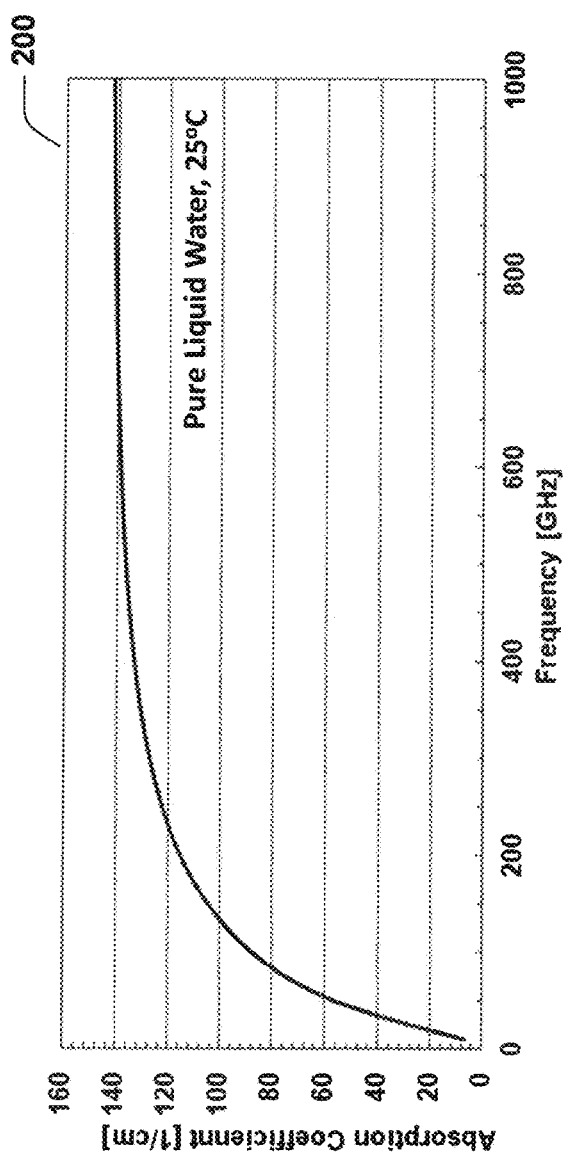
FIG. 2A
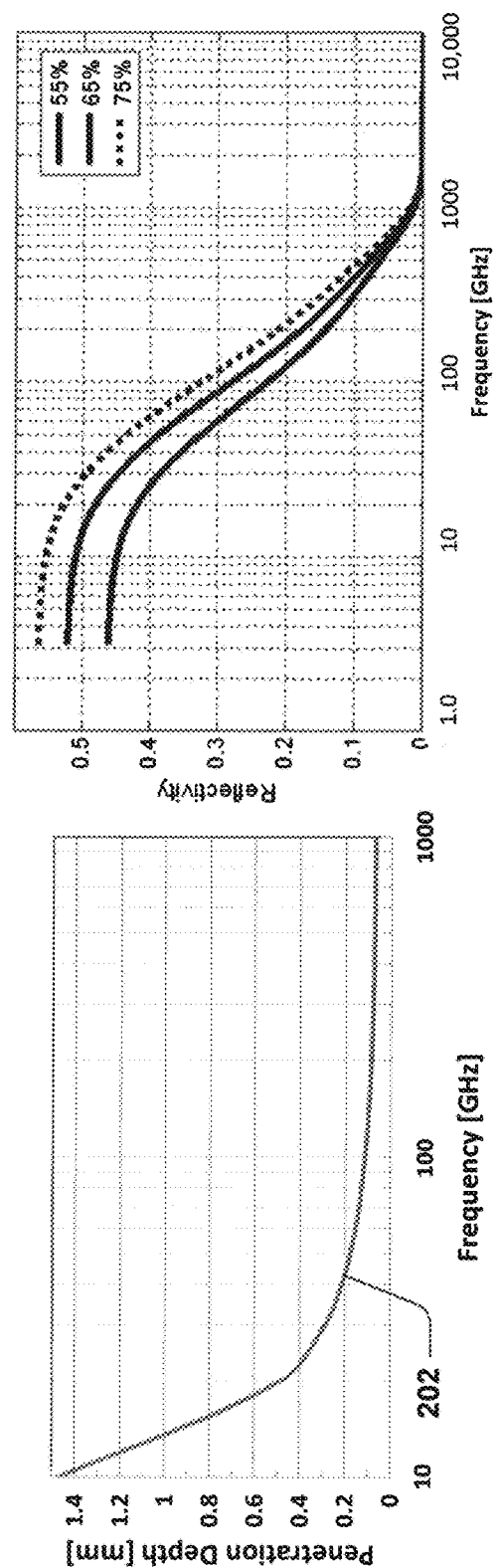
FIG. 2B
FIG. 2C

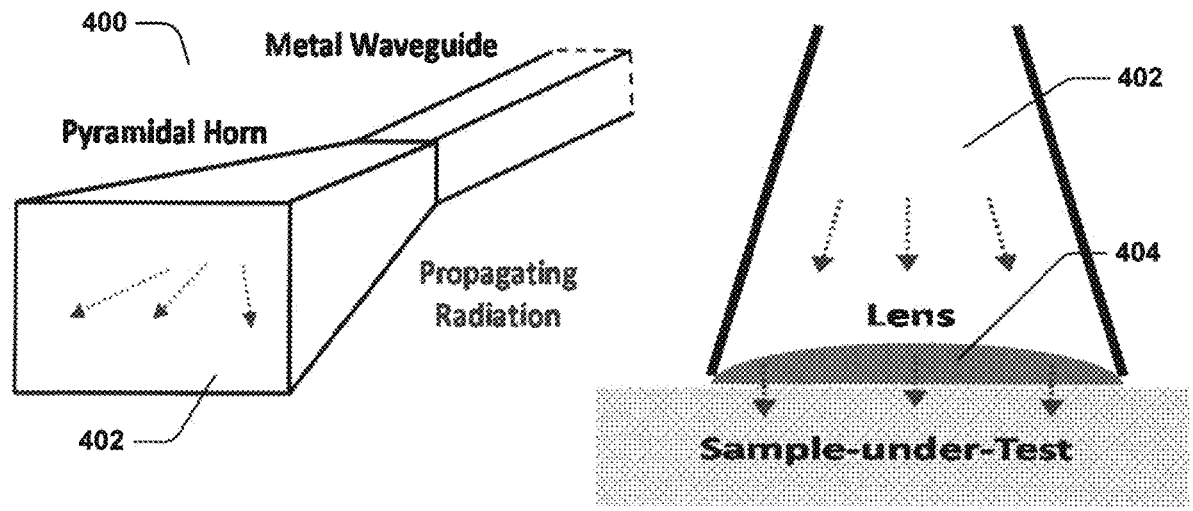
FIG. 4A
FIG. 4B
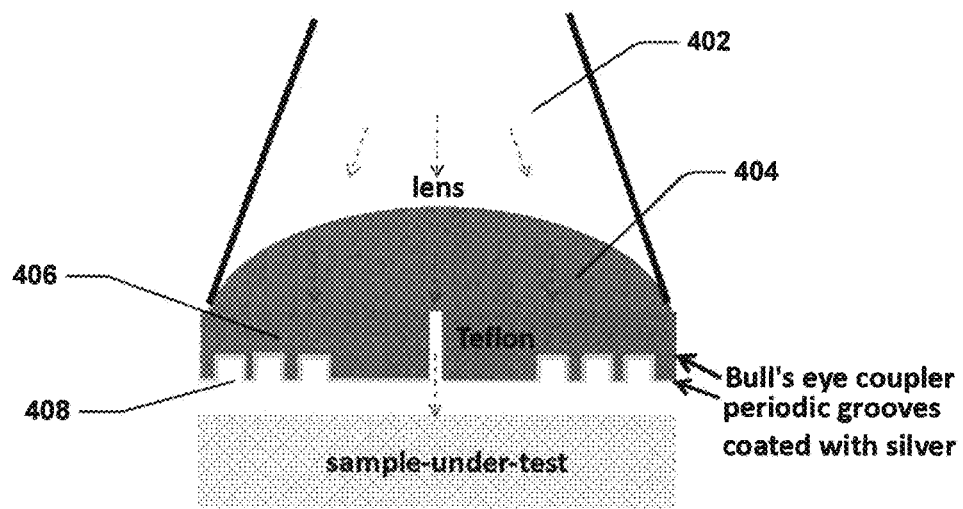
FIG. 4C

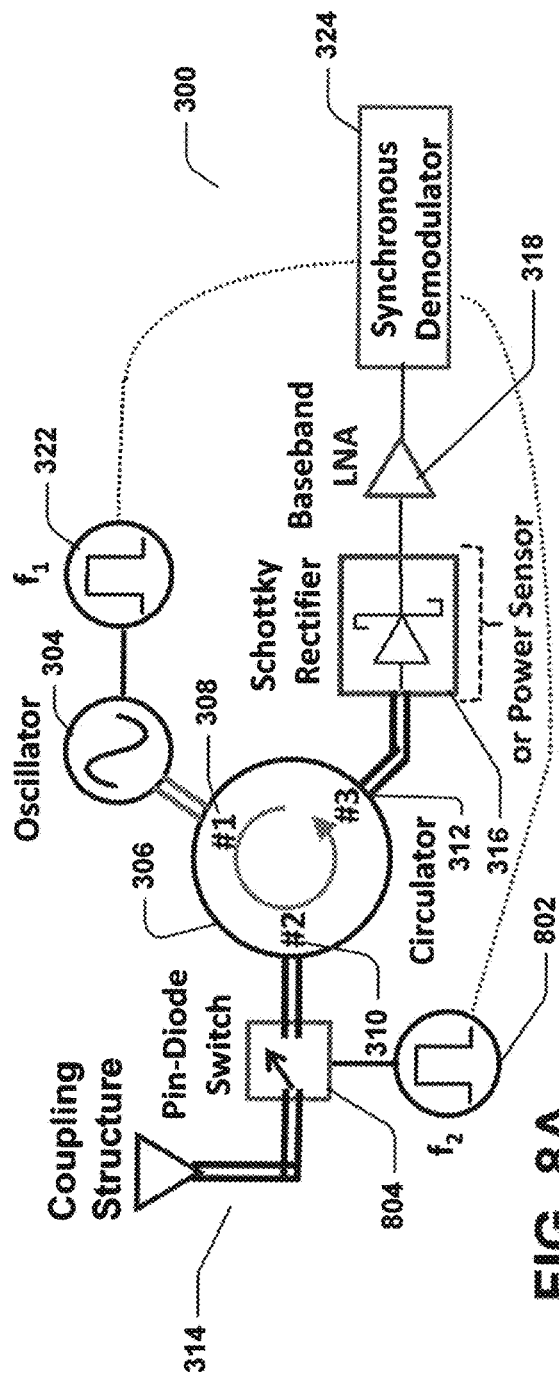
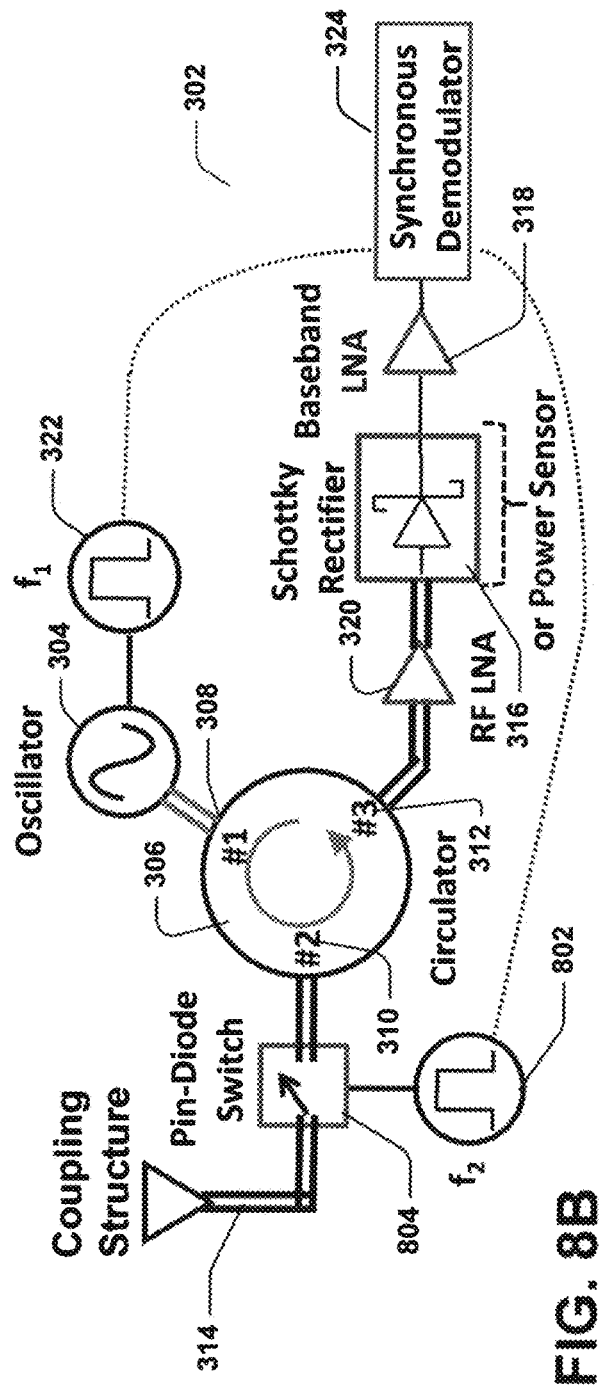
FIG. 8A
FIG. 8B

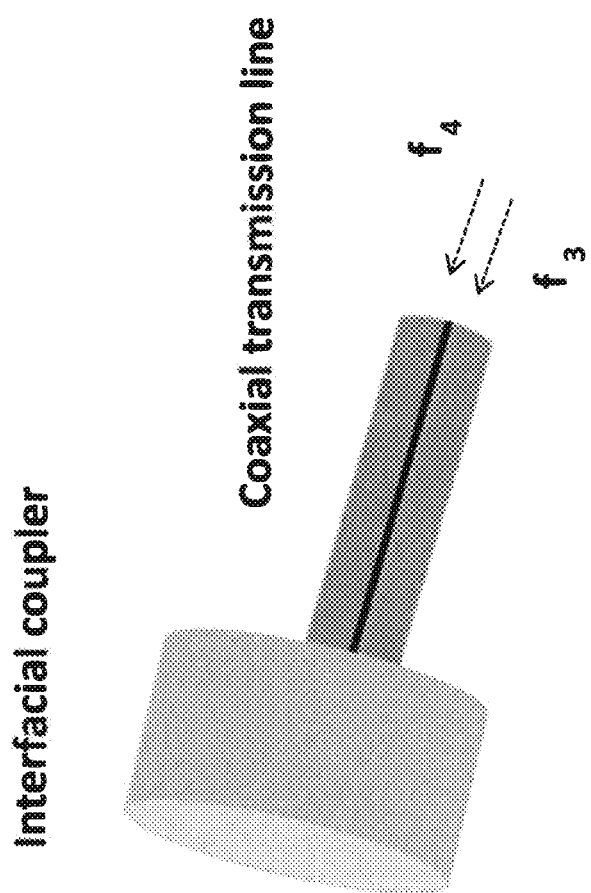

HYDRATION SENSOR

CROSS-REFERENCE TO RELATED APPLICATIONS

This application claims the benefit of U.S. Provisional Patent application Ser. No. 62/458,285 entitled "HYDRATION REFLECTOMETER" and filed Feb. 13, 2017. The entirety of the above-noted application is incorporated by reference herein.

This invention was made with government support under EY021590 awarded by the National Institutes of Health. The government has certain rights in the invention.

BACKGROUND

By most medical standards, the skin is considered an organ of the human body and carries out many vital functions such as thermal regulation and protection against external biological microorganisms. The dermis and epidermis vary in thickness greatly depending on location on the body. The epidermis varies from roughly 50-micron thick on "thin-skin" areas such as the eyelids, to over 1-mm thick on heavy-use areas such as the palms of the hands or soles of the feet. The average value around the entire body is roughly 100 micron. And the epidermis is a stratified squamous epithelial tissue, meaning that does not have its own blood supply. Instead, it relies solely on the blood supply from the dermis, which is its primary source of water and nourishment.

Independent of location on the body, the skin displays a characteristic variation of hydration with depth as illustrated in the hydration curve 100 in FIG. 1. Hydration is defined as the fraction of water in the skin tissue per unit mass, following the convention established for all "soft" tissue. More specifically, it is water in the aqueous state, not the "bound" state whereby water is chemically bonded to biomolecules (e.g., proteins) or other biological structures. The outermost sublayer of the epidermis, the stratum corneum, typically has about 20% hydration. This abruptly increases to approximately 60% in the innermost sublayer, the basale corneum. Once into the dermis, the hydration levels off to approximately 65% in a typical, healthy person, which is roughly the hydration level in soft tissue of all sorts.

Significant variations, however, can occur because of skin maladies or because of underlying disease. For example, skin burns introduce a lateral variation in hydration depending on the severity of the burn, be it $1^{st}$ degree (which damages only the epidermis), $2^{nd}$ degree (which extends into the dermis, either partially or fully), and $3^{rd}$ degree (damage into the subcutaneous). Carcinomas generally involve only the epidermis, and melanomas usually start in the epidermis but then grow vertically into the dermis where they can readily metastasize through the blood supply there (which is why melanomas are more deadly than carcinomas). Skin hydration can also be affected by internal disease, which affects the skin tissue through edema—the abnormality associated with leaking of blood vessels into surrounding soft tissue, which usually raises the fluid and hydration levels and leads to overall swelling. A common internal disease that causes this is congestive heart failure. Another is clot- or tumor-blockage of major blood vessels.

SUMMARY

The following presents a simplified summary in order to provide a basic understanding of some aspects of the innovation. This summary is not an extensive overview of the innovation. It is not intended to identify key/critical elements or to delineate the scope of the innovation. Its sole purpose is to present some concepts of the innovation in a simplified form as a prelude to the more detailed description that is presented later.

In one aspect of the innovation, a sensor is provided that includes a circulator having a plurality of ports, a coherent source coupled to a first port of the plurality of ports of the circulator, a power sensor or rectifier coupled to a second port of the plurality of ports of the circulator, an optional first low-noise amplifier between the circulator and the rectifier, a demodulator connected to the rectifier, and a coupling structure coupled to the a third port of the circulator, the coupling structure configured to couple radiation to a sample under test as a guided wave.

To accomplish the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

BRIEF DESCRIPTION OF THE DRAWINGS

FIG. 2A is an absorption coefficient of liquid water graph in accordance with an aspect of the innovation.

FIG. 2B is a penetration depth vs frequency curve in accordance with an aspect of the innovation.

FIG. 2C is a reflectivity of human skin graph in accordance with an aspect of the innovation.

FIG. 4A is a perspective view of a pyramidal waveguide horn antenna in accordance with an aspect of the innovation.

FIG. 4B is a cross section view of the pyramidal horn of FIG. 4A coupled to the sample under test through a collimating lens in accordance with an aspect of the innovation.

FIG. 4C is a cross-sectional view of a "Bulls-eye" coupling structure located flush to the bottom side of the collimating lens and enabling sub-wavelength spatial resolution.

FIGS. 8A and 8B illustrate schematic example embodiments of a hydration sensor in accordance with an aspect of the innovation.

FIG. 10 is perspective view of one or the other of the two interfacial couplers in FIGS. 6A and 7A connected to a coaxial transmission line in which electromagnetic energy at two separate frequencies $f_3$ and $f_4$, is incident, reflected, and subsequently processed.

DETAILED DESCRIPTION

Figure 1:
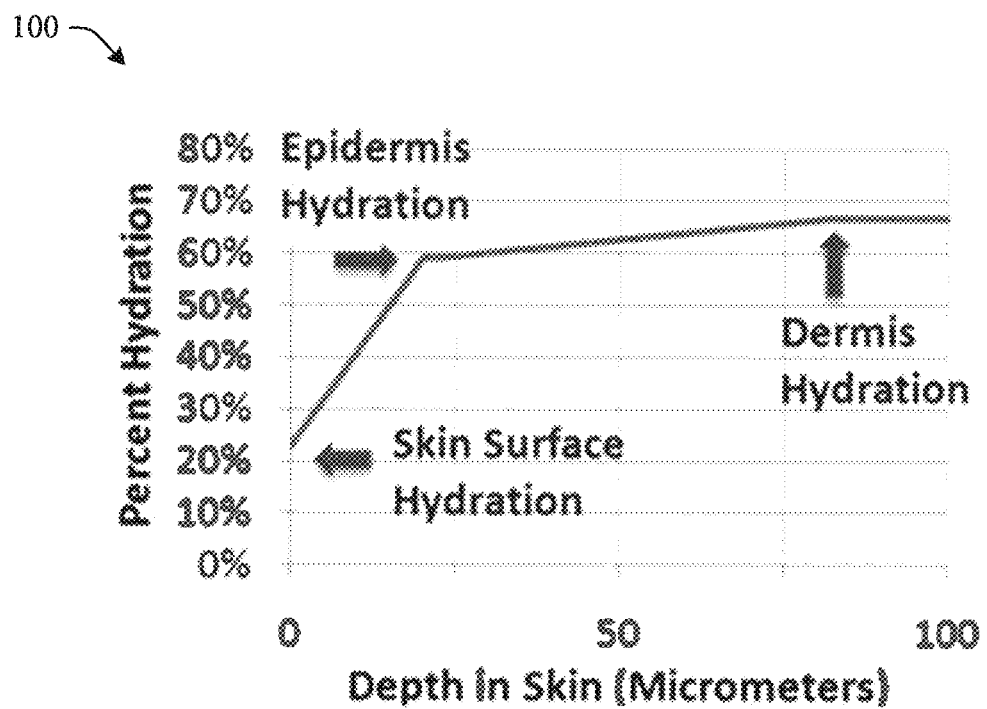
FIG. 1 is hydration curve illustrating hydration levels of the human skin in accordance with an aspect of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

While specific characteristics are described herein (e.g., thickness, orientation, configuration, etc.), it is to be understood that the features, functions and benefits of the innovation can employ characteristics that vary from those described herein. These alternatives are to be included within the scope of the innovation and claims appended hereto.

While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

Given this simple picture of skin physiology and pathology, a logical method of skin malady detection is one that can measure hydration through the epidermis and some distance into the dermis. The hydration can then be used to determine the presence of skin maladies through models, such as a stratified-medium dielectric-constant model. If hydration is measured for penetration well into the dermis, the presence of melanoma and other maladies can be determined.

However, many of these skin maladies occur on a size scale smaller than the wavelength of common electromagnetic radiation. A good example is tumors of melanoma in its early stages. So it is important that the sensor have sub-wavelength spatial resolution and can provide imagery by manual scanning or some other method.

Skin is an organ of the human body with a varying degree of reflectivity depending on hydration and other biological composition, and its location relative to soft tissue or the bone below it. The medical field has known that hydration is an important factor of human health, perhaps even a "vital sign." The innovation provides systems and methods for determining the hydration level (through skin models) on a whole body or specific locations of a body. The systems and methods can achieve an accuracy of approximately 1%. The systems and methods sample the epidermis and dermis through the introduction of low-level, non-ionizing electromagnetic energy either as guided-wave radiation incident perpendicular to the skin layers, or as electric or magnetic fields from interfacial (capacitive or inductive) couplers. The systems and methods determine the hydration level depending on the form of the energy: (1) through a more accurate measurement of the electromagnetic reflectance in the millimeter-wave region, for example in W band (75-110 GHz) or Ka band (26-40 GHz), and/or (2) through a more accurate measurement of the electromagnetic impedance change of interfacial couplers. The reflectance of the radiation is measured and mapped back the hydration level through electromagnetic modeling of the skin tissue or calibration ("look-up") tables. In some embodiments, in the millimeter-wave frequency region, the reflectance is sensitive to the hydration level because of the high magnitude of the dielectric constant of liquid water, be it in a pure or physiological form.

In some embodiments, a guided-wave coupling includes near-field capability, which results in an improved spatial resolution (e.g., approximately 1 mm). The technological method is to utilize either a "Bulls-eye" structure, or a fundamental-mode metal waveguide to direct coherent radiation onto the skin-under-test.

In some embodiments, an interfacial coupling provides comparable spatial resolution depending on the frequency and the proximity. For mm-wave frequencies and close proximity to the skin, an interfacial coupler may provide finer spatial resolution than 1 mm. A significant advantage of the interfacial coupling over the guided-wave coupling is the use of coaxial transmission line described in detail below. In some embodiments, the coaxial line works well up to roughly 100 GHz.

In some embodiments, for both types of coupling, the reflected energy is measured by placing a circulator or directional coupler between the source and the skin-under-test. The circulator can be a three-port, non-reciprocal device. The circulator can facilitate distinguishing between incident radiation and reflected radiation based on port locations. In some embodiments, the radiation is introduced to first port, a human skin sample to a second port, and the receiver (or detector) is coupled through a third port. The power detected in the third port is proportional to the reflectance in second port. The power coupling in the second port can occur either through a horn antenna, an open-ended waveguide, or an interfacial coupler. The horn antenna facilitates contact-free coupling to the skin having a diffraction-limited resolution of approximately several millimeters to one centimeter. The open ended waveguide facilitates contact coupling to the skin with "near-field", sub-wavelength resolution of approximately 1 mm. The interfacial coupler facilitates contact or proximity-contact sub-wavelength resolution of 1 mm or less.

The described coupling methods can facilitate whole-body hydration assessment or measurement for skin-malady diagnoses and vital-sign sensory applications. These facilitate, for example, body hydration mapping as applied to physical examinations, burn and skin cancer imaging, and other human malady sensing.

The depth-dependent hydration illustrated in FIG. 1 has been studied with respect to electric current flow and electromagnetic propagation (i.e., radiation). Incident radiation can come from outside the body and propagate perpendicular to the skin. Minimizing incident radiation such that there is little or no radiation transmitted through the body at frequencies below x-ray facilitates improves the accuracy of measures. Minimizing incident radiation can be achieved due to strong absorptive attenuation by liquid water, and/or strong scattering from soft and hard tissue.

FIG. 2A illustrates an absorption coefficient α plot 200 of liquid water in the frequency range of interest using a double-Debye model. The model is determined to be accurate at radio frequencies up to at least 600 GHz. For example, at 600 GHz, the absorption coefficient $\alpha \approx 140$ $cm^{-1}$, which means that the penetration depth $\delta \equiv 1/\alpha \approx 70$ micron. Soft tissue is about 65% hydrated and therefore can support greater penetration depth; the penetration depth is not high enough to get through the centimeter-scale or greater paths offered by a body. Thus, the innovation provides systems and methods to detect hydration level through reflected radiation.

The layered nature of the epidermis and upper dermis can be used to construct a stratified-media model to thereby predict the reflectivity in the skin tissue. From the stratified-media model in conjunction with the Bruggeman effective-medium model and the physiological hydration curve 100 illustrated in FIG. 1, a penetration depth vs frequency curve 202 can be obtained as illustrated in FIG. 2B. At frequencies around 500 GHz, the penetration depth is not great enough to reach the dermis on many parts of the human body. The curve 202, however, also shows that deeper penetration can be achieved by lowering the frequency to approximately 100 GHz or less. The trade-off between these two frequencies is illumination area and spatial resolution. Using ordinary antennas or quasi-optics, and free-space coupling, the illumination area on the skin from a transmitter is determined by the diffraction limit $d \sim 2.44 \, f \cdot \lambda$, where d is the diameter of an illumination spot, f is the f-number of the antenna or optics, and λ is the free-space wavelength. For standard antennas, such as pyramidal or diagonal horns, and standard free-space optics, the lowest practical f is approximately 1.0. In some embodiments, for 600 GHz radiation (λ=0.5 mm), the minimum spot diameter is ≈1.2 mm. In other embodiments, for 100 GHz radiation (λ=3.0 mm), the minimum spot diameter is ≈7.3 mm.

A related issue is magnitude of reflectivity. The larger the magnitude of reflectivity, the easier it is to measure. In particular, a larger magnitude of reflectivity eases the effects of physical noise. A stratified-media model can be used to compute the magnitude of reflectivity as a function of frequency. A plot 204 is illustrated in FIG. 2C. The plot 204 is parameterized by mean hydration through the epidermis; i.e., the mean value over approximately the first 75 microns in FIG. 1. From the plot 204, operation of the hydration sensor at 100 GHz enjoys three times the reflectivity as 600 GHz. The signal-to-noise ratio of a reflective sensor can be three times more sensitive. FIG. 2C further depicts a rapid increase in reflectivity with decreasing frequency to approximately 20 GHz, below which rate of increase decreases to values approximately 0.5.

Figure 3A:
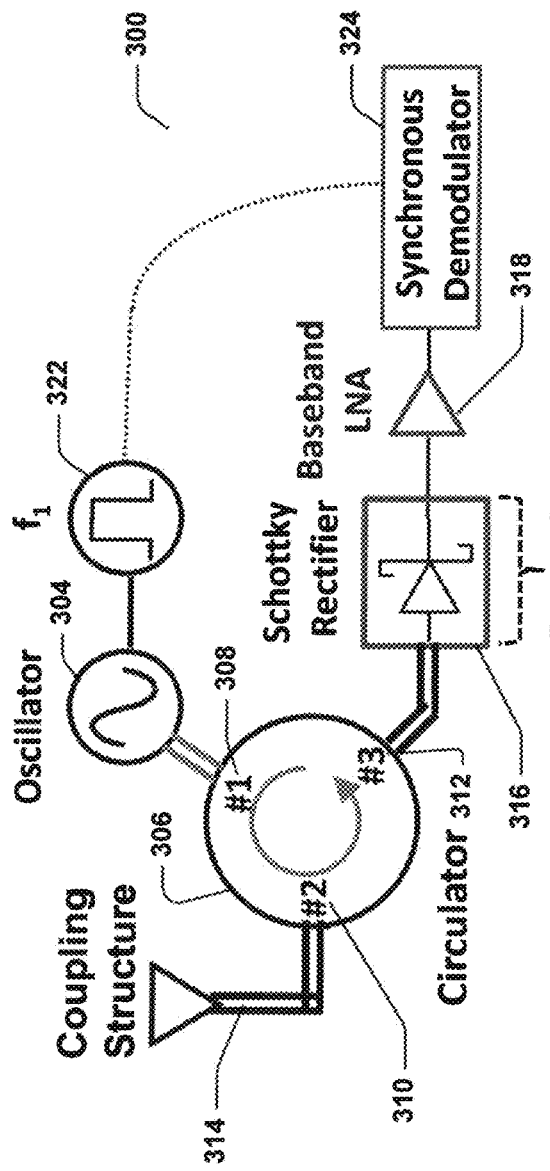
FIGS. 3A and 3B illustrate two example embodiments of a hydration sensor in accordance with an aspect of the innovation.
Figure 3B:
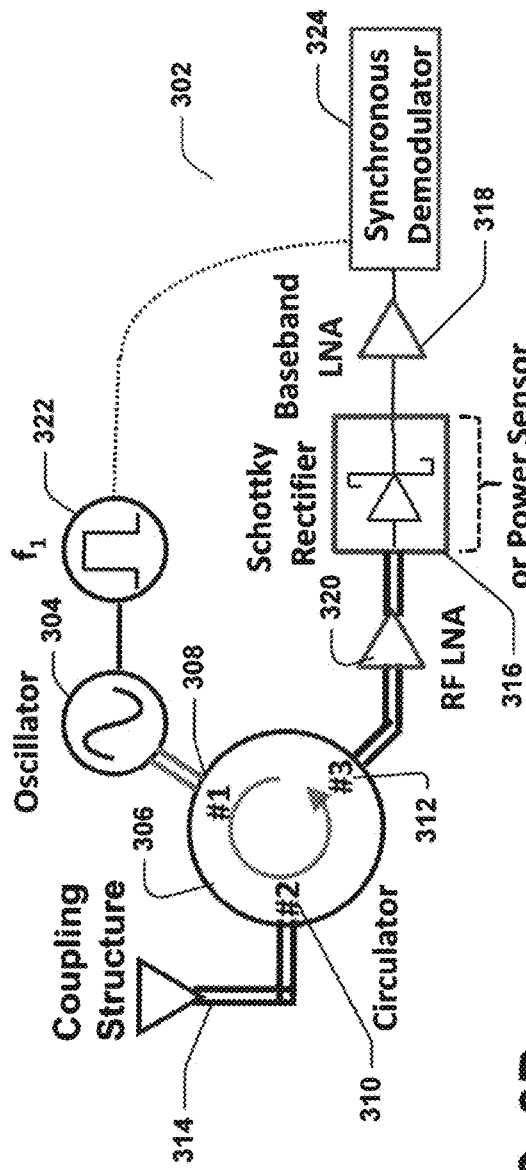

FIGS. 3A and 3B illustrate two example circuit embodiments of hydration sensors 300, 302 in accordance with an aspect of the innovation. The hydration sensors 300, 302 achieve measurements approximately 1% more accurate or better (in measuring hydration). The hydration sensors 300, 302 can mechanically scan quickly (e.g. seconds) to measure large areas of the human body and be compatible within a clinical (medical) setting. In some embodiments, the hydration sensors 300, 302 can be a waveguide design.

The hydration sensors 300, 302 include an oscillator 304 that is utilized as a coherent source. The oscillator 304 can be amplitude modulated and coupled to a metal waveguide of having a dimension and a bandwidth. The oscillator 304 is coupled directly to a waveguide based circulator 306. In some embodiments, the circulator 306 can have a first port 308, a second port 310, and a third port 312.

In some embodiments, the oscillator 304 is an electromagnetic non-reciprocal device in which radiation propagates in one helicity (e.g., clockwise or counter-clockwise). For example, the example hydration sensors 300, 302 utilize a counter-clockwise propagating helicity. This facilitates that radiation entering the first port 308 will propagate to the second port 310 but not the third port 312. Similarly, radiation entering the second port 310 will propagate to the third port 312 but not the first port 308. In embodiments, each port of the circulator 306 is extractive, e.g. radiation propagating with the correct helicity will exit the next port it encounters after entering the circulator 306. Once through the port and into a connected waveguide or transmission line, the radiation will not enter the circulator 306 again unless it encounters an impedance mismatch. Under an impedance mismatch, some of the radiation reflects from the mismatch back into the same port and enter the circulator 306 a second time with the allowed helicity.

The first port 308 of the circulator 306 is connected to the oscillator 304 via a transmission line. The second port 310 is coupled to a sample under test (SUT), e.g. skin via a coupling structure 314. In some embodiments, the second port 310 is coupled to the SUT either through a waveguide or coaxial transmission line. The SUT creates reflected radiation that propagates back into the circulator through the second port 310. The reflected radiation enters the circulator 306 through the second port 310 and is subsequently extracted out of the third port 312. The radiation exits the third 312 and into detector electronics that create a detector output signal (Xs) that is proportional to the reflected power. In some embodiments, the reflected power can be a function of the hydration (H) such that Xs=F(H). Given a calibration of the reflection described in detail below, the inverse of the function can be used to find H, which is H=G(Xs) where $G=F^{-1}$. The functions are dependent on the SUT. In some embodiments, the calibration depends on the manner by which radiation is coupled to the SUT.

Different coupler structures 314 (or couplers) may be used for different roles. FIGS. 4 and 5 illustrate guide-wave couplers. FIGS. 6 and 7 illustrates interfacial couplers. The guided-wave couplers of FIGS. 4 and 5 are differentiated from the interfacial couplers of FIGS. 6 and 7. The guided-wave couplers irradiate the skin with propagation electromagnetic radiation and then collect the reflected radiation from the skin in proportion to its reflectivity. In contrast, the interfacial couplers are sensitive to the skin through its effect on the impedance. The change of impedance then changes the reflected energy incident on the coupler from the second port 310 in the hydration sensors 300, 302.

Interfacial couplers, described in detail below, provide an additional benefit of providing higher spatial resolution sensing of the skin tissue than the guided-wave couplers. In some embodiments, an inductive interfacial coupler is used having impedance sensitive to changes in the magnetic permeability in the surrounding region. Magnetic fields will penetrate deeper into the skin than electric fields, which are governed by the electric permittivity. The electric permittivity is large in magnitude and has significant imaginary part for water and soft tissue of all sorts, which are why the absorption coefficient is relatively large and the penetration depth relatively small in the plots in FIGS. 2A and 2B.

In some embodiments, an important concern for a sensor is sensitivity. In some embodiments, sensitivity can be quantified as a minimum-detectable reflectivity (MDR) difference. The MDR can be affected by physical noise in detection electronics. The detection electronics can include a Schottky rectifier 316 (or other power sensor) followed by a baseband low-noise amplifier (LNA) 318. With continuing reference to FIGS. 3A and 3B, sensitivity can be affected by thermal noise and shot noise in the Schottky rectifier 316 and/or in the baseband LNA 318. The combination of the Schottky rectifier 316 and baseband LNA 318 creates an overall detector noise factor.

In some embodiments, the MDR is expected to be finer with guided-wave couplers than interfacial couplers. In particular, it is much finer than an inductive interfacial coupler as illustrated in FIG. 7. Hence, there can be an engineering trade-off presented by the coupling method chosen, the trade-off being between MDR, spatial resolution, and depth-of-penetration.

In the example hydration sensor 302 illustrated in FIG. 3B, the hydration sensor 302 includes a receiver having a radio frequency (RF) LNA 320 followed by the Schottky rectifier 316. In some embodiments, the RF LNA 320 has been developed to W band and beyond using monolithic microwave integrated circuit (MMIC) technology. A secondary benefit of a MIMIC LNA is superior impedance matching. Schottky rectifiers can be reactive at high frequencies, so they reflect some of the incident power from the third port 312 back into the circulator 306.

Independent of how radiation propagates out of the circulator 306, there is a function of effectively coupling it to the SUT. The manner in which this is done depends on the chosen spatial resolution, depth of resolution, and the measurement time. In some embodiments, a directive antenna such as a waveguide horn 400 shown in FIG. 4A can be used to achieve a spatial resolution of many wavelengths with relatively short measurement time. Ideally the antenna 400 has a high directivity in only one direction and the antenna 400 is oriented so that this direction is perpendicular to the surface of the SUT (i.e., "normal incidence"). Under this condition, most of the radiation reflected from the SUT will be retrodirective and therefore efficiently coupled back into the antenna 400. In some embodiments, the horn antenna 400 can be made more directive (i.e., collimated) by filling its opening 402 with a lens 404, as illustrated in FIG. 4B. In some embodiments, a plano-convex lens can be used as the lens 404. In some embodiments, the lens 404 may be made of a plastic such as Teflon; the planar side of the lens 404 mates well to flat SUTs and is biochemically inert.

Referring to FIG. 4C, in some embodiments, a bull's-eye coupler 406 can achieve spatial resolutions of approximately one wavelength or less. The bull's-eye coupler 406 can be placed flush with the flat side of the convex lens 404. The bull's-eye coupler 406 has a pattern of concentric circular grooves 408. In some embodiments, the entire (or substantially the entire) grooved side of the bull's-eye coupler 406 is coated with a metal film except in a small central disc. The grooves 408 act to concentrate the incident radiation into the disc by constructive interference of surface currents excited on the metal film. In some embodiments, the diameter of the disc should be less than a wavelength, but not so small as to make the coupling efficiency impractically low. An approximate range of the disc diameter d is $\lambda/10 < d < \lambda/4$. In some embodiments, an approximate number of concentric grooves 408 is 5 to 10.

In other embodiments, a sub-wavelength antenna can achieve spatial resolutions of approximately one wavelength or less when placed in close proximity to the SUT such that the SUT is illuminated with near-field radiation. In some embodiments, the sub-wavelength antenna is a Hertzian dipole.

The effective use of the bull's-eye coupler 406 requires that it be placed with the central disc in close proximity to the SUT to achieve sub-wavelength spatial resolutions. This is also "near-field" coupling. In some embodiments, the central disc can susceptible to moisture, oil, or other organic material. In this embodiment, a thin plastic film can be used on the grooved side to protect it against contamination of the central disc. This also prevents the metal film from tarnishing when the SUT is human skin, for example.

Figure 5A:
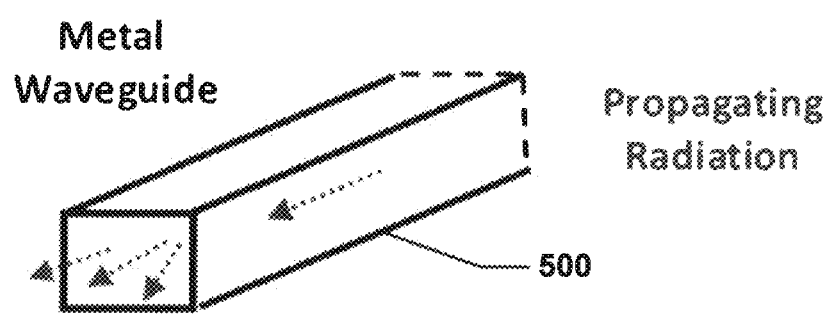
FIG. 5A is a perspective view of a rectangular metal waveguide displaying near-field coupling from the open waveguide end in accordance with an aspect of the innovation.
Figure 5B:
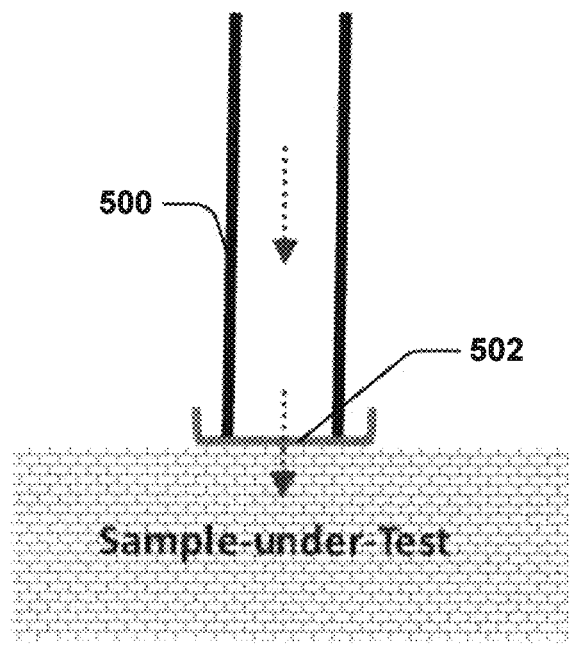
FIG. 5B is a side view of the open-ended waveguide in contact with a sample under test but separated from it by a thin membrane in accordance with an aspect of the innovation.

FIG. 5A illustrates an open-ended metal waveguide 500. The open-ended waveguide 500 is capable of achieving sub-wavelength resolutions. The open-ended waveguide 500 can be a type of "near-field" coupling that is used in close proximity to the SUT, as shown in FIG. 5B. The close proximity is made possible by a dielectric membrane 502 thin enough to provide efficient coupling without losses, but thick enough to chemically isolate the waveguide from the SUT. The spatial resolution for this approach can depend on waveguide dimensions. For example, for a "W band" (75-110 GHz) coupler, the standard waveguide is WR-10 having dimensions 0.05 inch×0.10 inch (height×width). Using an operating frequency of 100 GHz, the wavelength is $\lambda=3$ mm, for which the WR-10 dimension are $\approx 0.4 \cdot \lambda \times 0.8 \cdot \lambda = 2.9$ mm$^2$. In some embodiments, the membrane can be made of one of several different elastic plastics. The plastics can be highly transparent at RF frequencies (including the W band), and many of which are chemically inert. For example, the membrane can be made of Latex plastic.

The reflected signal level can be calibrated to determine the reflectivity of the SUT accurately. This can be achieved by replacing the SUT with a sample where the reflectivity is known to be unity, or close thereto, and is called a calibration sample (CAS). The form of the CAS depends on the method used. In some embodiments, the CAS will provide greatest accuracy if it acts as a "short circuit" element in the transmission line or waveguide. In some embodiments, a flat metal plate can accomplish the calibration when replacing the SUT in FIGS. 4B and 5B for the low- and high-resolution coupling methods, respectively. In some embodiments, the CAS can be made of aluminum. In other embodiments, alternative metals having high electrical conductivity can be used.

During calibration, the CAS produces a signal Xc at the detector that should always be larger in magnitude than the signal Xs from the SUT because it reflects essentially all of the radiation impinging on it from the second port 310. The reflectivity of the SUT can be estimated as $R \approx Xs/Xc$. The isolation structures, e.g. lens 404 or membrane 502, will leak a small amount of the radiation laterally so that Xc is a bit smaller than ideal. However, this is also true for Xs when the SUT is measured, so the error is canceled to first order.

In some embodiments, for radar, an antenna 314 is connected to the second port 310 which is a transmit port such that radiation entering the second port 310 from the oscillator 304 encounters the first significant reflection at the SUT in free-space. The reflected radiation from the SUT comes back to the second port 310 and re-enters the circulator 306 where it is subsequently extracted out by the third port 312 and detected by a receiver that includes the Schottky rectifier 316 and baseband LNA 318. In some embodiments, the oscillator 304 is modulated such that it radiates short pulses with a low duty cycle. The modulation can be performed by a modulator at frequency f1 322. The modulator facilitates determining the reflectivity of the SUT and its distance (i.e., "range") from the sensor, by measuring the amplitude and time-of-flight using sensitive time-domain instruments (e.g., an oscilloscope) in the third port 312. After the Schottky rectifier 316 and the baseband LNA 318, the output is detected by a synchronous demodulator 324. The synchronous demodulator 324 is locked to the modulator 322 frequency to facilitate accurate and noise-free detection.

Figure 6A:
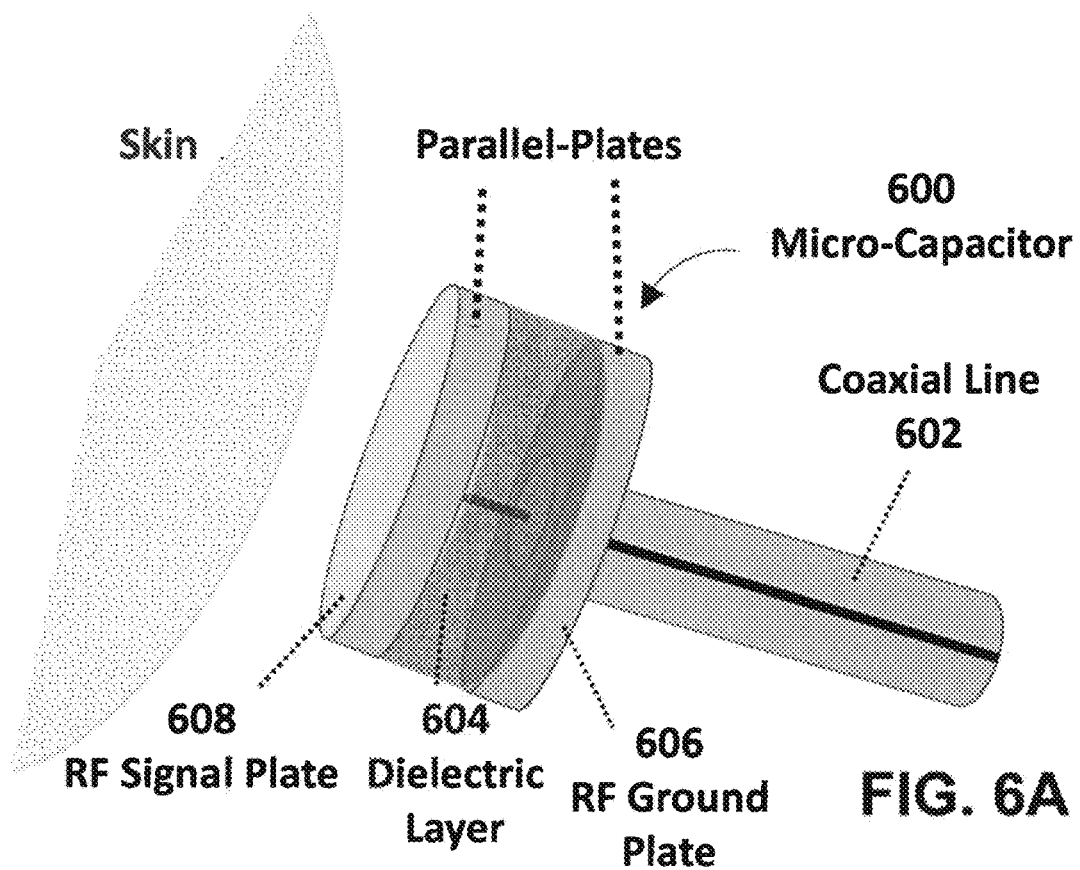
FIGS. 6A and 6B are perspective views of a coupling structure for hydration sensing consisting of a sub-wavelength interfacial micro-capacitor.
Figure 6B:
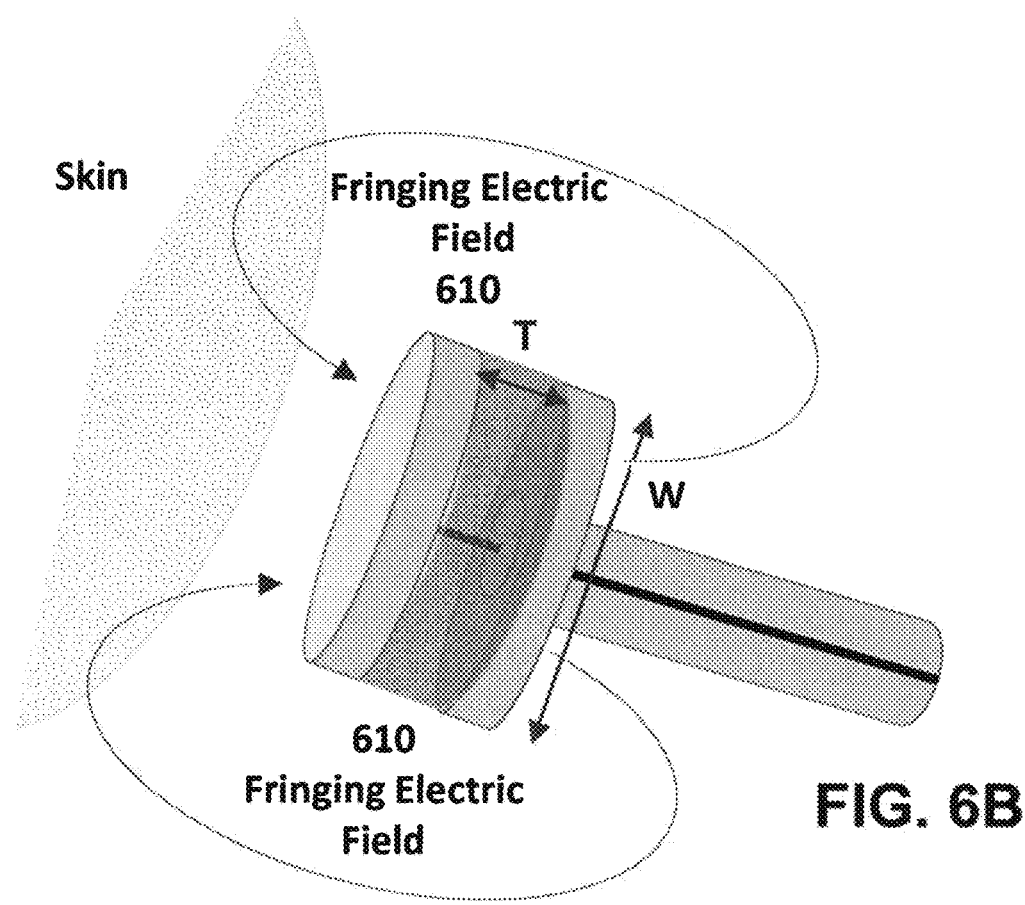

FIGS. 6 and 7 illustrate interfacial couplers. FIGS. 6A and 6B display a micro-capacitor 600 and a coaxial transmission line 602 which connects the micro-capacitor to the second port 310 of the circulator 306. The coaxial transmission line 602 includes an outer conductor and a center conductor. The micro-capacitor 600 includes parallel metal plates separated by a dielectric layer 604. A ground plate 606 is connected to the outer conductor of the coaxial transmission line 602. A signal plate 608 is connected to the center conductor of the coaxial transmission line 602.

The micro-capacitor 600 has a thickness-to-width (T/W) ratio depicted in FIG. 6B. In some embodiments, the T/W ratio can be approximately 1.0 or greater. The micro-capacitor 600 creates fringing electric fields 610 between the signal plate 608 and the ground plate 606. The fringing electric fields 610 make the capacitance of the micro-capacitor 600 sensitive to the surrounding medium. In particular, the capacitance is sensitive to a SUT when the micro-capacitor is brought into close proximity. The hydration state of the SUT affects the fringing effect of the fringing fields 610 and the absolute value of the RF capacitance accordingly. By measuring the impedance or reflectivity of the capacitor in the circuits 300 or 302, the hydration level can be derived. In some embodiments, the dielectric layer 604 can be chosen to have RF electrical properties that support the fringing effect and therefore the change in capacitance per unit change in hydration. The dielectric property of concern is the complex dielectric constant, $\varepsilon = \varepsilon' + j\varepsilon''$, where $\varepsilon'$ is the real part and $\varepsilon''$ is the imaginary part. In some embodiments, the dielectric material has low absorptive losses (i.e., $\varepsilon'' \ll \varepsilon'$) and a small real part ($\varepsilon'$ just over 1.0) to enhance the fringing effect. In some embodiments, the dielectric material is an artificial (e.g., humanmade) dielectric material, such as a plastic.

Figure 7A:
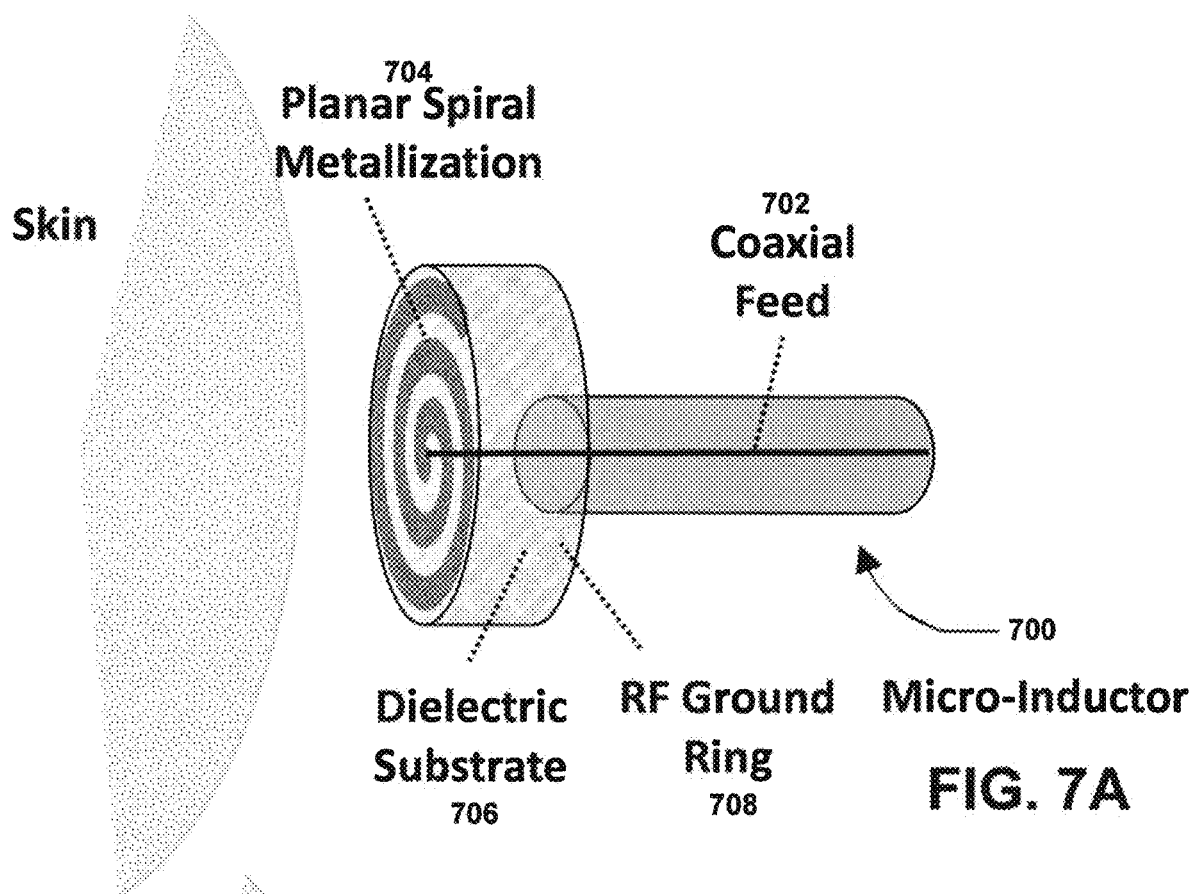
FIGS. 7A and 7B are perspective views of a coupling structure for hydration sensing consisting of a sub-wavelength interfacial micro-inductor.
Figure 7B:
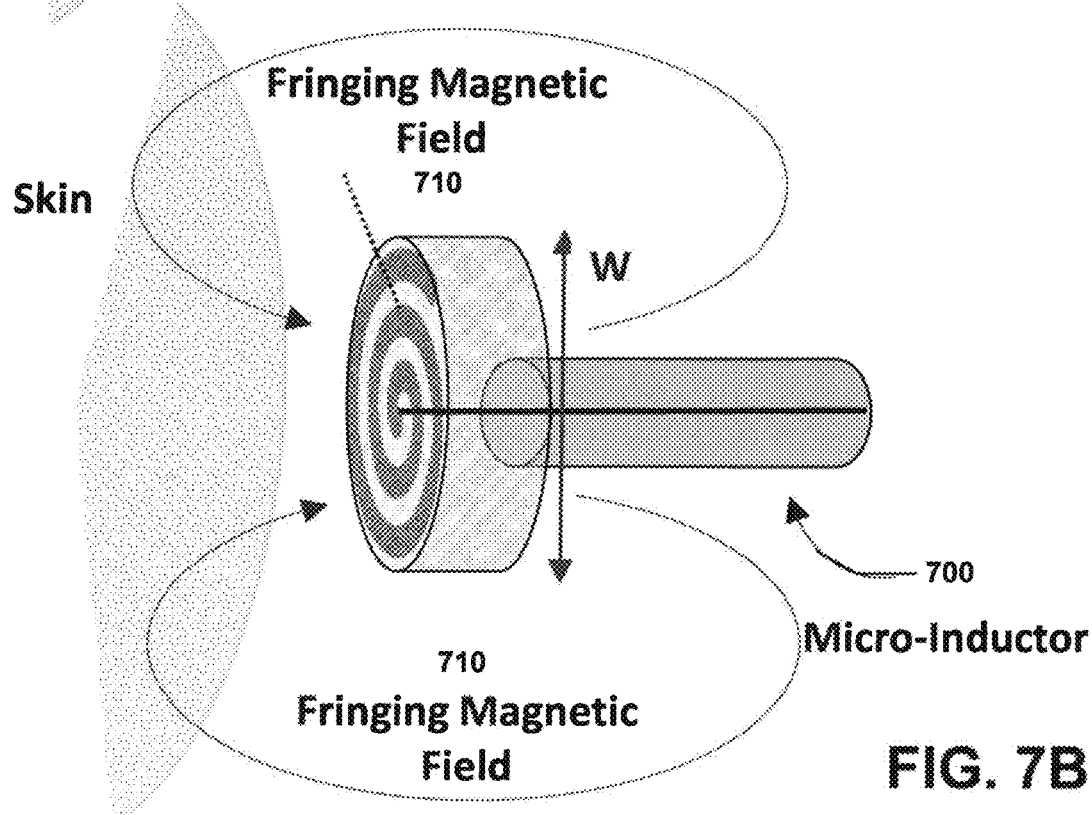

FIGS. 7A and 7B includes a micro-inductor 700 and a coaxial transmission line 702 which connects the micro-inductor 700 to the second port 310 of the circulator 306. The micro-inductor 700 includes a planar spiral inductor 704 mounted on a dielectric substrate 706 contained inside a ground ring 708. The outer termination of the planar spiral inductor 704 is electrically connected to the ground ring 708 which in turn is connected to a ground conductor of the coaxial transmission line 702. The inner termination of the planar spiral inductor 704 is connected to a center conductor of the coaxial transmission line 702. The micro-inductor 700 creates a magnetic field 710 having magnetic field lines as in FIG. 7B. The micro-inductor 700 radiates a higher magnetic-to-electric field ratio than the micro-capacitor 600. Soft tissue such as skin is generally non-magnetic in nature (except for a small effect from blood). The magnetic field 710 is not attenuated as strongly in skin tissue as the electric field 610. The overall electromagnetic radiation from the micro-inductor 700 can penetrate deeper than that of the micro-capacitor 600. Hydration can be determined by measuring the change of impedance or reflectivity via the electrical inductance. In some embodiments, the micro-inductor 700 may be less sensitive to hydration changes than the micro-capacitor 600; however, the greater penetration depth of the micro-inductor 700 will offer a trade-off between the micro-inductor 700 and the micro-capacitor 600. Magnetic fields are generally not affected by electrical permittivity (i.e., dielectric constant). The material type of the dielectric substrate 706 is not as critical as for the dielectric layer 604 of the micro-capacitor 600 in FIG. 6. In some embodiments, a dielectric substrate 706 having a moderate $\varepsilon'$ and low $\varepsilon''$ can be used.

The micro-capacitor 600 and the micro-inductor 700 provide high spatial resolutions compared to the "near-field" techniques based on waveguide or Bull-eye-lens coupling of FIGS. 4 and 5. This is because the resolution is determined by the physical width W, and W can be made relatively small compared to a wavelength, rendering deep-subwavelength spatial resolutions possible. In some embodiments, spatial resolutions in the range $\lambda/100 < W < \lambda/10$ can be achieved for practical free-space wavelengths of excitation, $\lambda$.

Referring to FIGS. 8A and 8B, and continuing reference to FIGS. 3A and 3B, the hydration sensors 300, 302 can be address leakage radiation issues to better improve the accuracy of the hydration sensors 300, 302. In some embodiments, the hydration sensors 300, 302 can be more demanding in some respects than the typical radar because the SUT is much closer to the circulator 306 than a typical radar target. The proximity makes it impractical to form short pulses. Furthermore, the hydration sensors 300, 302 can be susceptible to leakage radiation that propagates around the circulator 306 opposite to the preferred helicity, meaning propagation from the first port 308 to the third port 312 in addition to the desired second port 310. Generally the leakage power is just a few percent or less of the preferred power; however the leakage can compromise the accuracy.

In some embodiments, with reference to FIGS. 8A and 8B, the hydration sensors 300, 302 can be augmented with a second modulator 802 to amplitude modulate the power in the second port 310 with a different frequency $f_2$, in addition to amplitude modulating the oscillator 304 with the first modulator 322 having a frequency $f_1$. In some embodiments, one or both of f1 and f2 can be "baseband" frequencies, i.e., much less than the oscillator 304 frequency. In this embodiment, the hydration sensors 300, 302 include a pin diode switch 804. The pin-diode switch 804 modulates the RF power between the circulator port 310 and the coupling structure 314. Thus, FIGS. 8A and 8B illustrate additional example embodiments of a hydration sensor 300 with an RF LNA, and a hydration sensor without an RF LNA followed by the Schottky rectifier (or other power sensor). The reflected power from the SUT will be double-modulated, and the power that goes from the first port 308 to the third port 312 (i.e., the "leakage" power) will be single-modulated. Using standard techniques of signal processing, analog or digital, the double-modulated power received in the third port 312 via the SUT port 310 can be discriminated from the single-modulated leakage power from the first port 308, and the effect of leakage can be corrected with post processing.

It is to be understood that all aspects of the invention described above are amenable to operation in other regions of the electromagnetic spectrum besides the millimeter-wave region. From the tissue-interaction radiative phenomenology described in FIG. 2, there are two advantages to operate the hydration sensor at different frequencies. In some embodiments, THz-frequency components can attain better spatial resolutions than W-band component in proportion to the operating wavelength due to higher operating frequencies, e.g. 300 GHz and above or the THz region of the spectrum. For example, a 550-GHz centered sensor system has approximately 5.7 times the spatial resolution as a 94-GHz system. In some embodiments, such an operating frequency can utilized for corneal hydration sensing and/or other applications.

For many applications such as the whole-body hydration mapping described below, operating frequencies below the millimeter-wave region may become attractive for two reasons. First, there is greater penetration into the skin as seen in the plot of FIG. 2B. For example, at operation around 10 GHz, the penetration depth becomes several millimeters. In regions on the body where the skin is relatively thick, this means that the hydration can be measured deep into the dermis. This is important because the dermis is the layer where skin maladies are often critical. For example, the treatment of skin burns is simple if the burn damage goes partially into the dermis, but may require surgical intervention (i.e., grafting) if the damage goes deep into the dermis or into the subcutaneous layer. Similarly, other skin disorders such as edema, a frequent problem in patients subject to long hospitalization, involve significant increases in hydration levels in the dermis. A second reason for lower frequency operation is cost and complexity. As a general rule in RF electronics, the power and overall performance of devices and components improve significantly as the frequency goes down.

Figure 9A:
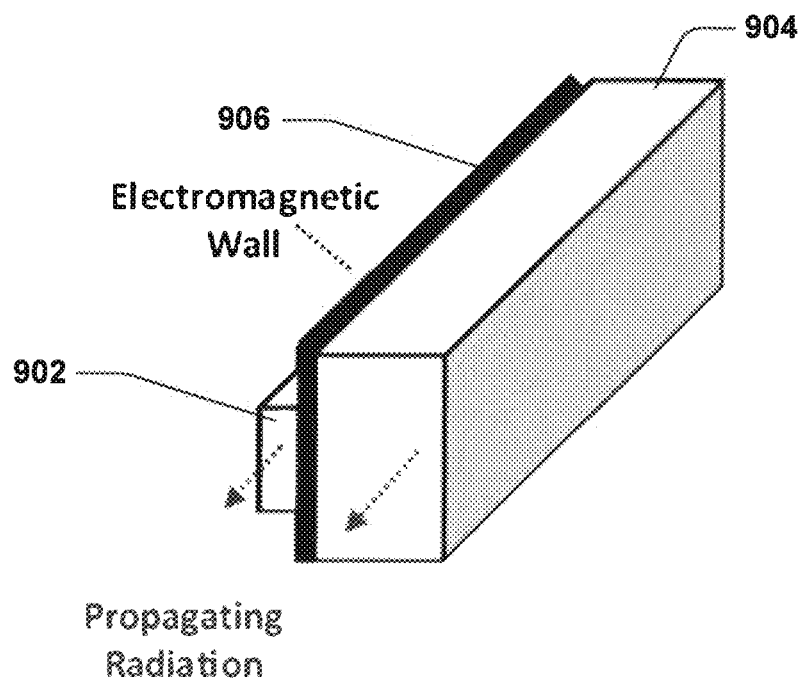
FIG. 9A is a perspective view of a double-waveguide near-field coupling structure in accordance with an aspect of the innovation.
Figure 9B:
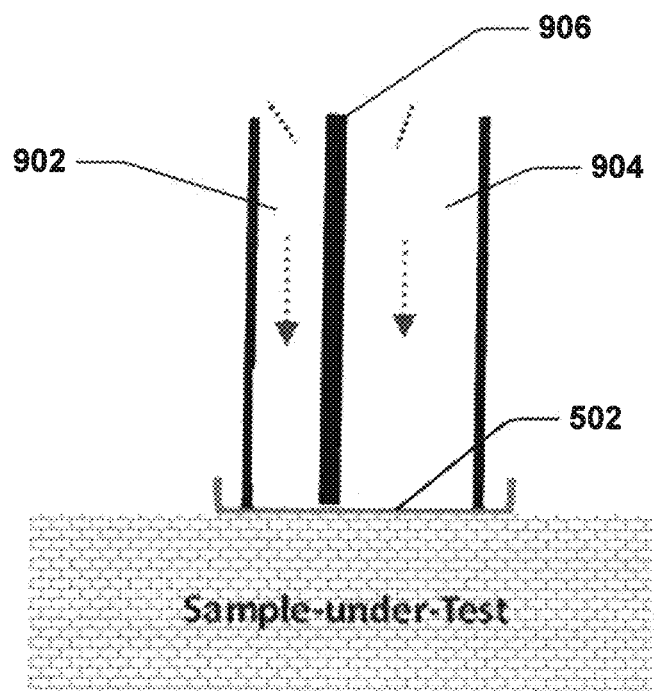
FIG. 9B is a side view of the double-waveguide, near-field coupling structure in accordance with an aspect of the innovation.

The simplicity of the sensor schematic designs in FIGS. 4A and 4B or FIGS. 8A and 8B, along with the compactness of the near-field waveguide coupling in FIG. 5, lend themselves to multiple-frequency operation. For example, two-frequency operation could be carried out as shown in FIGS. 9A and 9B. The near-field coupling is done by two adjoined waveguides 902 and 904. In some embodiments, the waveguides 902, 904 are rectangular or substantially rectangular in shape. The first waveguide 902 can propagate the frequency $f_3$ and the second waveguide 904 can propagate the frequency $f_4$ where it was assumed $f_3 < f_4$ (note: these are the frequencies of the oscillators 304, not the modulation frequencies). In some embodiments, the contact between both waveguides 902, 904 and the SUT can be through a membrane 502 approach as in FIG. 5B. The electronic components for frequencies $f_3$ and $f_4$, whether the design of FIGS. 3A and 3B or FIGS. 8A and 8B, can be integrated compactly because they are all packaged in a waveguide, which has very low radiation cross-coupling. In some embodiments, the two frequencies can be complementary in the sense that the $f_3$ radiation will have greater depth of penetration but lower spatial resolution than the $f_4$ radiation. This facilitates estimation of the size of a hydrated target, such as a tumor or cyst.

One challenge with the two-frequency coupling would be mutual coupling. With enough frequency separation between $f_3$ and $f_4$, it would be easy to isolate $f_3$ from the second waveguide 904 by a cutoff mechanism. In some embodiments, rectangular waveguides can have a critical frequency fc below which there is no propagation, e.g. a cutoff. So if $f_3 < fc$, low mutual coupling can occur from the second waveguide 904 to the first waveguide 902. However, $f_4$ can then propagate in the first waveguide because metal waveguides may have higher-order spatial modes in which higher frequencies than $f_3$ can propagate. Hence, isolation can be accomplished using an electromagnetic wall 906. In some embodiments, the electromagnetic wall 906 is a thin layer of a magnetic conductor such as iron or mu-metal.

In some embodiments, three or more frequencies can be used and operated in three or more different waveguides respectively. In other embodiments, separate frequencies within a same waveguide can be accomplished using frequency sweeping or hopping techniques.

With reference to FIG. 10, in some embodiments using interfacial coupling, multiple-frequency (or a pulsed) operation is possible when a micro-capacitor and/or a micro-inductor are designed to employ broadband frequencies. Because a coaxial transmission line is inherently broadband for its fundamental (TEM) mode, two fundamental modes with frequencies $f_3$ and $f_4$ respectively can be fed to the interfacial couplers (as shown in FIGS. 6 and 7) through a common coaxial transmission line. More than two frequencies are also possible using the interfacial coupler and coaxial transmission line.

In some embodiments, the schematic diagrams of FIGS. 3A and 3B or FIGS. 8A and 8B can be integrated on a printed-circuit board or similar packaging technology. Printed circuit boards can be used for implementations of at least 30 GHz. In other embodiments, as the frequency approaches 100 GHz, monolithic integration can be used to form MMICs. In particular, monolithic integration can be used for RF LNAs are employed as in the designs of FIG. 4B or FIG. 8B. In some embodiment, MMICs are fabricated from silicon, GaAs, or another semiconductor to obtain different performances and costs. In some embodiments, the circulator 306 is made of a magnetic material such as ferrite. The circulator 306 operates with a permanent magnet or electromagnet nearby which is facilitated with printed circuit board implementations.

Figure 11A:
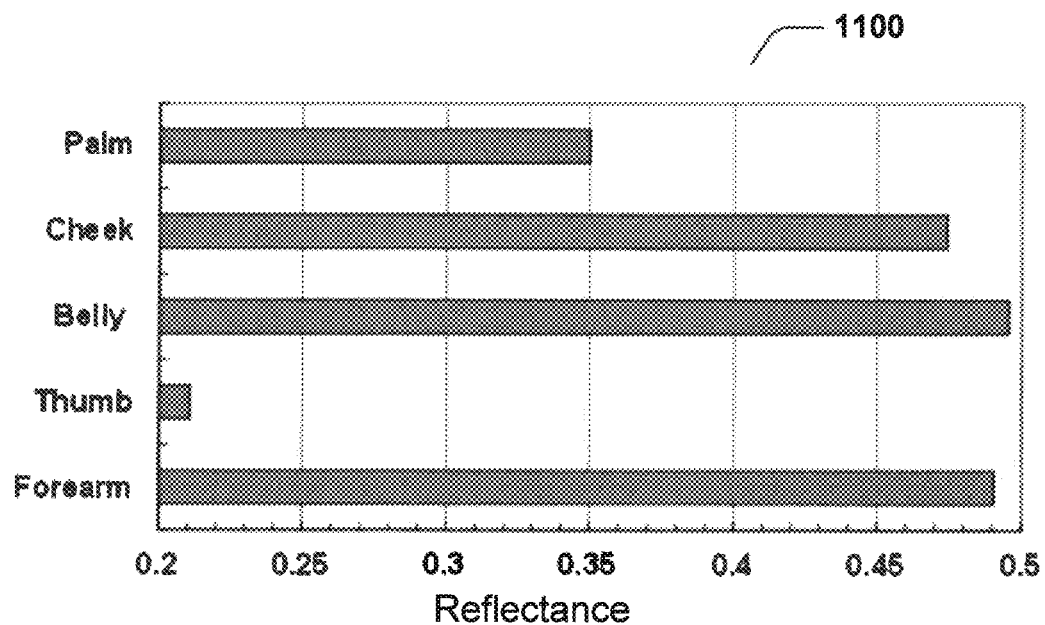
FIGS. 11A and 11B are graphs illustrating hydration sensor experimental results of human skin using a 94 GHz (W band) coherent source along with a Schottky rectifier and a power sensor, respectively, in accordance with an aspect of the innovation.
Figure 11B:
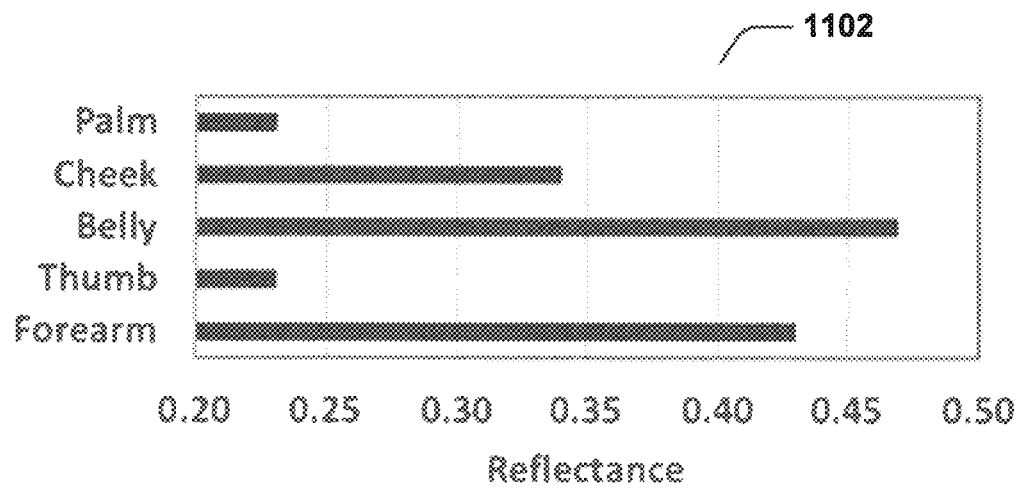

In one experimental embodiment, the oscillator 304 was a 94-GHz Gunn diode mounted in a WR-10 waveguide. The circulator 306 was fabricated in WR-10 and had an isolation of ~15 dB. The detector 316 was a WR-10-mounted Schottky rectifier. Experimental tests were conducted on voluntary human subjects measuring the reflectivity at various parts of the human body relative to an aluminum-plate acting as the CAS. The results are illustrated in a bar chart 1100 in FIG. 11. In another experimental embodiment, the WR-10-mounted Schottky rectifier was replaced with a WR-10 waveguide power sensor and reflectances were measured. The results are illustrated in a bar chart 1102 in FIG. 11B.

Figure 12:
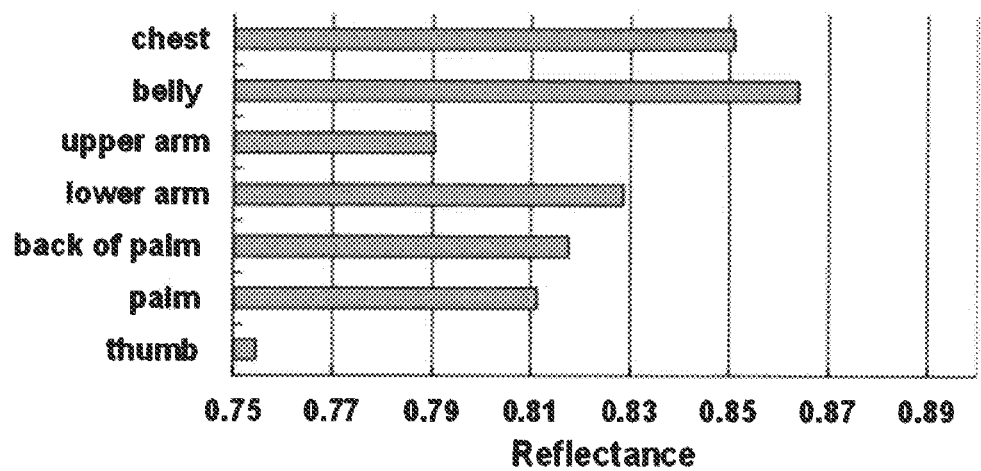
FIG. 12 is a graph illustrating experimental for reflectivity sensing results of human skin using a 30 GHz (Ka-band) coherent source along with a Schottky-rectifier detector in accordance with an aspect of the innovation.

In another experimental embodiment, to demonstrate experimental performance with lower frequency and much greater penetration into skin tissue, a 30 GHz (Ka-band) hydration sensor based on the design of FIG. 4A and the high-resolution coupling of FIG. 5B was assembled. The oscillator 304 was a 30-GHz Gunn diode mounted in WR-28 waveguide. The circulator 306 was packaged in WR-28 waveguide and had an isolation of ~20 dB. The detector 316 was a WR-28-mounted Schottky rectifier. It was demonstrated on voluntary human subjects, measuring the reflectivity at various parts of the body relative to an aluminum-plate acting as the CAS. The results are illustrated in the bar chart 1200 in FIG. 12.

Figure 13A:
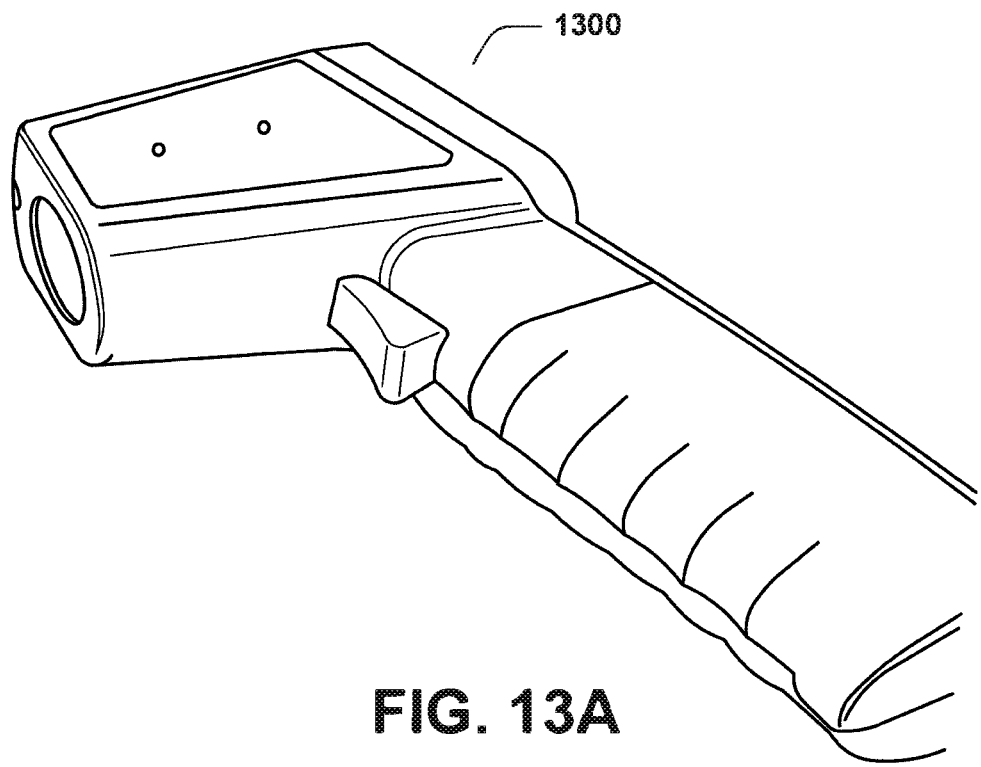
FIG. 13A is an example embodiment of a hydration sensor in accordance with an aspect of the innovation.
Figure 13B:
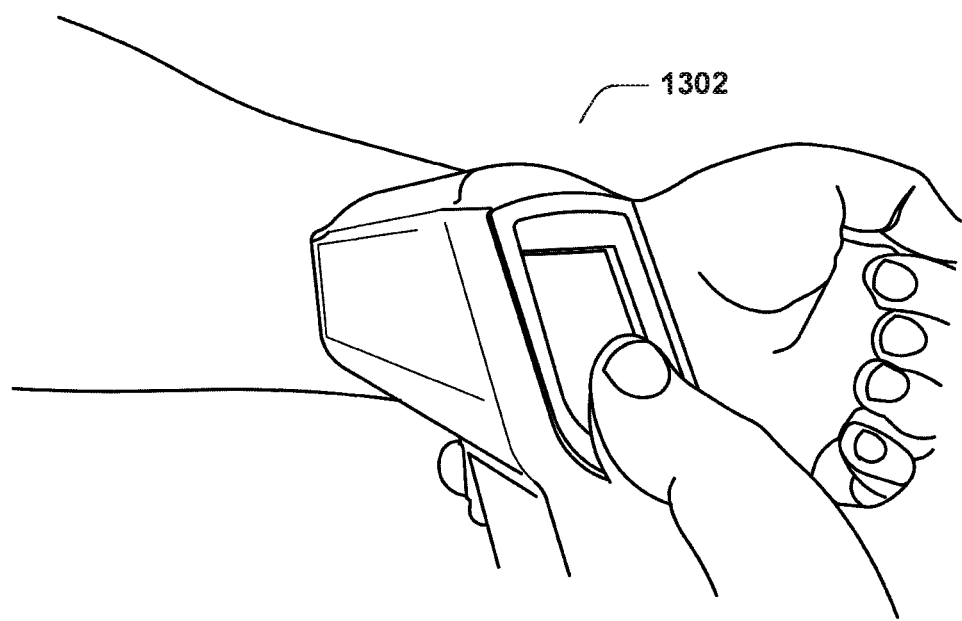
FIG. 13B is an example embodiment of a hydration sensor in operation in accordance with an aspect of the innovation.

FIG. 13A is an example embodiment of a hydration sensor 1300 that has a pistol-like shape including a battery compartment in a hand-grip. FIG. 13A shows the hydration sensor 1300 being coupled to a human forearm. Besides whole-body capability, the unit includes real-time visual display and wireless connection to a computer or smartphone of choice. Many embodiments exist for the layout of the components and electronics inside the pistol form.

The innovation provides unprecedented accuracy of hydration measurement (approximately 1%). Conventional techniques, such as dc skin resistance measurements, are less accurate. In addition, the innovation is non-invasive, whereas dc-based resistance techniques require a more intimate contact between the sensor and the skin. Further, the innovation allows for no contact (e.g., horn-coupled version) or a loose contact with the skin (e.g., near-field waveguide coupler or interfacial-coupler).

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A skin-hydration sensor comprising:
    a circulator having a plurality of ports;
    a coherent source coupled to a first port of the plurality of ports of the circulator and amplitude modulated at a first frequency;
    a coupling structure connected to a second port of the circulator, the coupling structure configured to couple to a skin sample under test without penetrating the skin sample;
    a detector coupled to a third port of the plurality of ports of the circulator; and
    a demodulator connected to the output of the detector.

2. The skin-hydration sensor of claim 1, wherein the coupling structure is a metal waveguide having an open end to couple with the skin sample under test.

3. The skin-hydration sensor of claim 1, further comprising:
    at least two adjoined open-ended waveguides to couple two or more separate frequencies.

4. The skin-hydration sensor of claim 1, further comprising:
    an RF-transparent membrane that covers the open end of the metal waveguide that couples to the skin sample under test.

5. The skin-hydration sensor of claim 1, wherein the coupling structure is an interfacial planar inductive coupler connected to coaxial transmission line configured to couple radiation to the skin sample under test.

6. The skin-hydration sensor of claim 1, further comprising:
    an RF low-noise amplifier disposed between the third port of the plurality of ports of the circulator and the detector.

7. The skin-hydration sensor of claim 1 further comprising:
    a baseband low-noise amplifier disposed between the detector and the demodulator.

8. The skin-hydration sensor of claim 1, wherein the skin-hydration sensor is miniaturized using integrated-circuit techniques.

9. The skin-hydration sensor of claim 1, wherein the coupling structure comprises a free-space bull's-eye lens located between a waveguide horn antenna and the skin sample under test.

10. The skin-hydration sensor of claim 9, further comprising an RF-transparent dielectric film that covers the bull's-eye lens.

11. The skin-hydration sensor of claim 1, wherein the coupling structure is an interfacial capacitor connected to a coaxial transmission line configured to couple radiation efficiently to the skin sample under test.

12. The skin-hydration sensor of claim 11, further comprising:
    the coaxial transmission line carrying two or more separate frequencies to the coupling structure.

13. The skin-hydration sensor of claim 1 further comprising:
    a pin-diode switch disposed between the coupling structure and the circulator, and configured for two-port amplitude modulation at a second frequency.

14. The skin-hydration sensor of claim 13, further comprising:
    a demodulator that demodulates an amplitude of a reflected signal at a first baseband frequency applied to the coherent source and at a second baseband frequency applied to the pin-diode switch to provide greater sensitivity for skin-hydration detection.

15. A method, comprising:
    connecting a coherent source to a first port of a circulator;
    amplitude modulating the coherent source at a first frequency;
    connecting a detector to a third port of the circulator to provide an output;
    connecting a coupling structure to a second port of the circulator, the coupling structure configured to couple to a skin sample under test without penetrating the skin sample;
    amplitude modulating a reflected signal with a two-port pin-diode at a second frequency; and
    demodulating the output of the detector with a demodulator disposed after the detector, wherein the demodulator demodulates at both the first and second frequencies.

16. The method of claim 15, wherein the coupling structure comprises
    a metal waveguide having an open end to the sample under test; and the method further comprises:
    covering the open end with an RF-transparent membrane.

17. The method of claim 15, comprising:
    disposing a baseband low-noise amplifier between the detector and the demodulator.

18. The method of claim 15, wherein the coupling structure comprises:
    coupling a bull's-eye lens between a waveguide horn antenna and the skin sample under test.

19. The method of claim 15, wherein the coupling structure comprises:

coupling an interfacial capacitor or an interfacial planar inductive coupler connected to a coaxial transmission line.

20. A system, comprising:

a circulator having a plurality of ports;

an oscillator coupled to a first port of the plurality of ports of the circulator and amplitude modulated at a first frequency;

a coupling structure connected to a second port of the circulator, the coupling structure configured to couple to a skin sample under test without penetrating the skin sample;

a pin-diode switch between the coupling structure and the circulator and modulated at a second frequency;

a detector coupled to a third port of the plurality of ports of the circulator; and a RF low-noise amplifier disposed between the circulator and the detector; and a demodulator, wherein the demodulator is connected to the output of the detector and demodulates at both the first and second frequencies.

* * * * *